United States Patent [19]
Schembri

[11] Patent Number: 5,591,643
[45] Date of Patent: Jan. 7, 1997

[54] SIMPLIFIED INLET CHANNELS

[75] Inventor: Carol T. Schembri, San Mateo, Calif.

[73] Assignee: Abaxis, Inc., Sunnyvale, Calif.

[21] Appl. No.: 115,162

[22] Filed: Sep. 1, 1993

[51] Int. Cl.[6] ................................................. B01D 21/26
[52] U.S. Cl. ............................ 436/45; 436/63; 436/177;
436/180; 422/64; 422/72; 422/101; 210/95;
210/198.1; 210/380.1; 210/514; 210/532.1;
210/782; 210/789
[58] Field of Search ............................... 422/64, 72, 101,
422/102; 436/45, 63, 177, 180; 210/95,
198.1, 360.1, 380.1, 745, 782, 789

[56] References Cited

U.S. PATENT DOCUMENTS

| | | | |
|---|---|---|---|
| 4,244,916 | 1/1981 | Guigan | 422/72 |
| 4,314,968 | 2/1982 | Guigan | 422/64 |
| 4,623,519 | 11/1986 | Cornut et al. | 422/72 |
| 4,689,203 | 8/1987 | Kaartinen et al. | 422/72 |
| 4,743,558 | 5/1988 | Guigan | 436/45 |
| 4,761,268 | 8/1988 | Andersen et al. | 422/72 |
| 4,876,203 | 10/1989 | Guigan | 436/45 |
| 4,894,204 | 1/1990 | Cornut | 422/72 |
| 4,902,479 | 2/1990 | Bri kus | 422/72 |
| 4,963,498 | 10/1990 | Hillman | 436/69 |
| 4,999,304 | 3/1991 | Robertson | 436/45 |
| 5,061,381 | 10/1991 | Burd | 210/789 |
| 5,071,625 | 12/1991 | Kelln et al. | 422/72 |
| 5,077,013 | 12/1991 | Guigan | 422/64 |
| 5,104,813 | 4/1992 | Besemer et al. | 436/179 |
| 5,122,284 | 6/1992 | Braynim et al. | 210/782 |
| 5,160,702 | 11/1992 | Kopf-Sill et al. | 422/72 |
| 5,173,193 | 12/1992 | Schembri | 210/782 |
| 5,173,262 | 12/1992 | Schembri | 210/782 |
| 5,186,844 | 2/1993 | Burd et al. | 210/782 |

OTHER PUBLICATIONS

Tech Update, "Blood Rotor Test Magic", *Popular Mechanics*, Feb. 1993.
Schembri, C., Abstract, "Centrifugation and Capillary Integrated into a Multiple Analyte Whole Blood Analyzer", Abaxis, Inc., Feb., 1993.
Marketing brochure, Abaxis, Inc., Aug. 1993.

*Primary Examiner*—Jill Warden
*Assistant Examiner*—Harold Y. Pyon
*Attorney, Agent, or Firm*—Townsend and Townsend and Crew LLP

[57] ABSTRACT

The present invention provides centrifugal rotors for delivering a liquid, typically a biological sample such as diluted plasma, to an unvented chamber in the rotor through an unmodified inlet channel. The unvented chamber is typically a cuvette comprising reagents necessary for analysis of a biological sample. The unmodified inlet channels are sized such that, as the rotor spins, gas escapes from the chamber through the inlet channel as the liquid enters the chamber through the inlet channel. The primary feature which allows the air to escape from the unvented chamber is that the cross sectional area of the inlet channel is greater than the cross sectional area of the liquid flowing through it.

9 Claims, 7 Drawing Sheets

SIMPLIFIED INLET CHANNELS

BACKGROUND OF THE INVENTION

The present invention relates generally to devices and methods for analyzing biological fluids. In particular, it relates to the design and use of improved centrifugal rotors which allow delivery of a biological sample or reagent to an unvented chamber in the rotor.

Biological tests of blood plasma and other biological fluids frequently require that fluids be quickly divided into predetermined volumes for analysis in a variety of optical tests or assays. It is also frequently desirable to separate potentially interfering cellular components of the material from the biological fluid prior to testing. Such measurement and separation steps have previously been typically performed by centrifugation to separate, for instance, blood plasma from the cellular components, followed by manual or automated pipetting of predetermined volumes of the blood plasma into separate test wells. Such procedures are labor intensive and time-consuming. As a result, various automated systems and methods have been proposed for providing multiple aliquots of plasma suitable for testing in a more efficient manner.

A major advance in the analysis of biological fluids has been the use of centrifugal rotors. These rotors are designed to measure volumes of a biological fluid, such as blood, remove cellular components, and mix the fluid with an appropriate diluent for optical testing. Typically, the rotors provide a plurality of discrete volumes of sample in separate cuvettes in which the sample is optically analyzed.

When the cuvettes are filling, it is important that individual cuvettes are completely isolated so that bubbles or chemical debris from one cuvette cannot be transferred to another. In addition, reliable methods for evacuating gas from the cuvettes must be devised so that air bubbles are not introduced into the cuvettes during filling. Such air bubbles may interfere with subsequent optical analysis of the sample.

The rotors capable of performing these functions should be capable of measuring and distributing relatively small volumes of liquid to a large number of cuvettes. The rotor design should be simple and amenable to low-cost manufacturing procedures. In particular, it is desirable for the rotors to be of unitary construction with no separable or movable parts. Liquid measurement and separation steps should be simple and take place in relatively short times. In particular, the methods should require relatively few steps and should be capable of being performed with little or no intervention or manipulations by the operator. It would be particularly desirable if the methods required only rotation of the rotor in order to effect measurement and delivery of the liquid. The present invention addresses these and other needs.

DESCRIPTION OF THE BACKGROUND ART

U.S. Pat. No. 4,244,916 discloses a rotor comprising a plurality of cuvettes positioned radially outward of a central receptacle. Each cuvette is connected to the central receptacle by a duct and comprises a separate air escape orifice. U.S. Pat. No. 4,314,968 relates to rotors having cells positioned on the periphery of the rotor. Each cell includes a peripheral orifice for removing fluid introduced into the cell. U.S. Pat. No. 4,902,479 discloses a multi-cuvette rotor comprising elongated, radially extending cuvettes. Each elongated cuvette comprises a first chamber for receiving a first constituent and a second chamber for receiving a second constituent. A divider structure between the first and second chambers prevents mixing of the constituents before a predetermined time. Mixing occurs as the rotor is spun at a sufficient speed. U.S. Pat. No. 4,963,498 discloses devices which rely upon capillaries, chambers, and orifices to pump and mix fluids for optical analysis. U.S. Pat. No. 5,077,013 discloses rotors comprising peripheral cuvettes connected to holding chambers positioned radially inward from the cuvettes.

SUMMARY OF THE INVENTION

The present invention provides centrifugal rotors for delivering a liquid, typically a biological sample such as diluted plasma, to unvented chambers in the rotor. The chambers are used to perform any of a number of functions, such as metering liquids, separating solid components from a sample, waste fluid isolation, or analysis of the sample. In the preferred embodiments, the chambers are cuvettes comprising reagents for the optical analysis of the sample. Alternatively, the chambers provide fluid isolation for waste fluids such as excess sample, excess diluent, and the like.

The rotors of the invention comprise unmodified inlet channels which are sized such that, as the rotor spins, gas escapes from the chamber through the inlet channel as the liquid enters the chamber through the inlet channel. An "unmodified inlet channel" as used herein refers to a simple inlet channel, typically having a rectangular cross section, which is not modified (e.g., by altering the cross-sectional shape, surface texture, and the like) to provide a pathway for gas to escape from a cuvette that is not otherwise vented.

The primary feature of the rotors of the invention which allows the air to escape from the unvented chamber is that the cross sectional area of the inlet channel is greater than the cross sectional area of the liquid flowing through it. The cross sectional area of the liquid flowing into the inlet channel is controlled by adjusting the resistance to flow of the channels which feed into the inlet channel.

One of skill will recognize that resistance to flow in a given channel will depend upon the liquid being transported through the channel. Resistance to flow of liquid in the channel can be adjusted in a number of ways. Typically, the geometry of the passage is used. Channels having a smaller cross section (as determined by width and/or depth) have greater resistance than those with larger cross sections. Also, lengthening a channel increases resistance to flow. Alternatively, the surface texture of the channel can be modified to increase or decrease resistance to flow.

In a typical embodiment, the inlet channels are positioned radially outward from a distribution channel. The distribution channel is connected to a delivery channel having high resistance to flow as result of a small cross sectional area. The delivery channel can be a straight or curved channel or a siphon. Typically, the ratio of the cross sectional area of the delivery channel to that of the inlet channel will be at least about 2:3, preferably at least about 1:2.

As a result of the high resistance to flow in the delivery channel, the cross sectional area of the liquid in the inlet channel will be less than that of inlet channel, itself. To provide sufficient venting, the ratio of the cross sectional area of the inlet channels to the cross sectional area of the liquid in them is greater than 2:1, preferably greater than about 4:1. The channel may also include vents through which the gas forced out of the unvented cuvettes is released.

DESCRIPTION OF THE PREFERRED EMBODIMENT

Figure 1:
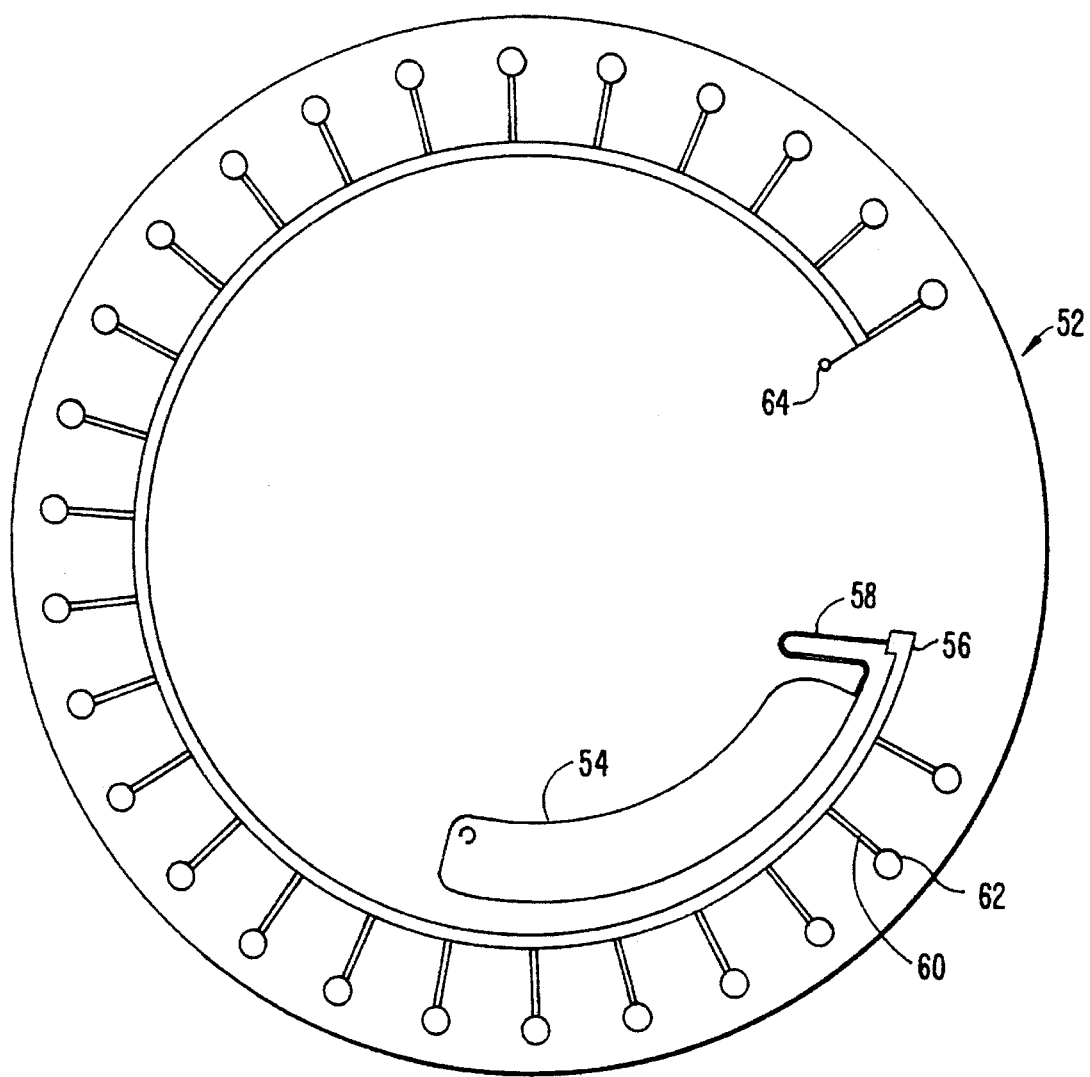
FIG. 1 is a top plan view of a rotor showing the unmodified inlet channel connected to a distribution ring and a delivery channel having a high resistance to flow as compared to the distribution channel and the inlet channels.

The present invention provides methods and devices for the delivery of liquids to chambers in an analytical rotor. The rotors of the invention are designed such that liquid flows into an unvented chamber through an simplified inlet channel which allows for the escape of trapped air in the chamber.

The rotors of the invention are suitable for the analysis of any liquid, typically a biological sample such as whole blood or plasma. It is also useful with numerous other biological fluids, such as urine, sputum, semen, saliva, ocular lens fluid, cerebral fluid, spinal fluid, amniotic fluid. Other fluids that can be tested include tissue culture media, food and industrial chemicals, and the like.

The rotors typically provide chambers which can separate cellular components from the biological sample (e.g. whole blood), measure a precise volume of liquid sample (e.g. plasma), mix the sample with an appropriate diluent and deliver the diluted sample to cuvettes for optical analysis. The fluid delivered to the cuvettes, undergoes reaction(s) within the cuvettes, e.g., reaction with a reagent which forms part of an analytical procedure to detect one or more analytes within the fluid. The sample may further be optically analyzed while present in the rotor, either with or without prior reaction.

The apparatus of the present invention comprises an analytical rotor having a rotor body which is capable of being mounted on a conventional laboratory centrifuge of the type which is commercially available from suppliers, such a Beckman Instruments, Inc., Spinco Division, Fullerton, Calif.; Fisher Scientific, Pittsburgh, Pa.; VWR Scientific, San Francisco, Calif., and the like. Generally, the centrifugal rotor will include a receptacle or other coupling device suitable for mounting on a vertical drive shaft provided by the centrifuge. The particular design of the receptacle or coupling device will depend on the nature of the centrifuge, and it will be appreciated that the centrifugal rotor of the present invention may be adapted for use with all or most types of centrifuges which are now available or which may become available in the future.

The rotor body comprises a structure which maintains a desired geometric pattern or relationship between a plurality of chambers, interconnecting passages, and vents, as described in more detail below. Various specialized chambers and channels suitable for use in the rotors of the invention are disclosed in U.S. Pat. Nos. 5,061,381 and 5,122,284, and U.S. Ser. No. 07/678,762 and 07/783,041 which are incorporated herein by reference.

Usually, the body will be a substantially solid plate or disk with the chambers and passages formed as spaces or voids in the otherwise solid matrix. Conveniently, such solid plate structures may be formed by laminating a plurality of separately-formed layers together into a composite structure where the chambers and horizontal passages are generally formed between adjacent layers. The vertical passages may be formed through the layers. The individual layers may be formed by injection molding, machining, or combinations thereof, and will usually be joined together, typically using a suitable adhesive or by ultrasonic welding. The final enclosed volumes are formed when the layers are brought together.

Of course, the centrifugal rotor could also be formed as a plurality of discrete components, such as tubes, vessels, chambers, etc., arranged in a suitable framework. Such assemblies of discrete components, however, are generally more difficult to manufacture and are therefore less desirable than those formed within a substantially solid plate.

The rotor body may be formed from a wide variety of materials and may optionally include two or more materials. Usually, the material(s) will be transparent so that the presence and distribution of the biological fluid, cellular components, and reagents, may be observed within the various internal chambers and passages. Optionally, to the extent analytical chambers, e.g., cuvettes, or other test wells are formed within the rotor, it is desirable to have suitable optical paths formed within the rotor so that the contents of the cuvettes may be observed spectrophotometrically, fluorometrically, or by other optical assessment instruments. The construction of suitable cuvettes having particular optical paths formed therethrough is disclosed in U.S. Pat. No. 5,173,193, the disclosure of which is incorporated herein by reference. In the preferred embodiment, the rotor is formed with an acrylic resin having suitable optical properties, at least in those areas which define an optical path.

The apparatus and method of the present invention are suitable for performing a wide variety of analytic procedures and assays which are beneficially or necessarily performed on blood plasma. The analytic procedures may require that the blood plasma be combined with one or more reagents so that some visibly detectable change occurs in the plasma which may be related to the presence and/or amount of a particular component (analyte) or characteristic of the plasma. Preferably, the plasma will undergo a reaction or other change which results in a change in color, fluorescence, luminescence, or the like, which may be measured by conventional spectrophotometers, fluorometers, light detectors, etc. In some cases, immunoassays and other specific binding assays may be performed within the cell-free fluid collection chamber or within cuvettes which are connected to the collection chamber. Generally, such assay procedures should be homogenous and not require a separation step. In other cases, however, it may be possible to accommodate heterogenous assay systems by providing a means to separate blood plasma from the collection chamber or another test well or cuvette after the immunological reaction step has occurred.

Conventional blood assays which may be performed include glucose, lactate dehydrogenase, serum glutamic-oxaloacetic transaminase (SGOT), serum glutamic-pyruvic transaminase (SGPT), blood urea (nitrogen) (BUN), total protein, alkalinity, phosphatase, bilirubin, calcium, chloride, sodium, potassium, magnesium, and the like. This list is not exhaustive and is intended merely as being exemplary of the assays which may be performed using the apparatus and method of the present invention. Usually, these tests will require that the blood and plasma be combined with one or more reagents which result in an optically detectable, usually photometrically detectable, change in the plasma. The reagents which are required are well known and amply described in the patent and scientific literature.

The reagents are preferably provided in lyophilized form to increase stability. Ideally, they are provided in the form of lyophilized reagent spheres as described in U.S. Ser. No. 07/747,179, which is incorporated herein by reference.

Referring now to FIG. 1, an analytical rotor comprising the chambers and channels of the present invention can be seen. FIG. 1 shows a rotor 52 having a sample chamber 54, positioned radially inward of a distribution channel 56. The sample chamber 54 can be used to perform any of a number of functions in the rotor, such as separation of cellular material from plasma, mixing biological sample with diluent, and the like. The sample chamber 54 is connected to the distribution channel 56 through siphon 58. At predetermined point in the analysis of the sample fluid, fluid flows through the siphon 58 into the distribution channel 56. Fluid in the distribution channel 56 is then delivered through the inlet channels 60 into the cuvettes 62. Siphon 58 is dimensioned such that the ratio of the cross sectional area of the inlet channels 60 to the cross sectional area of the liquid in them is greater than 2:1, preferably greater than about 4:1. The cross sectional area of the inlet channels 60 is typically the same as or slightly smaller than that of the distribution channel 56 so that gas in the unvented cuvettes escapes through the inlet channels 60 and distribution channel 56. If the sample is plasma or diluted plasma and the channels are rectangular in cross-section, their dimensions are typically as follows: siphon: 0.150 mm depth, 0.200 mm width; distribution channel 0.300 mm depth, 0.500 mm width; inlet channels: 0.150 depth, 0.500 width. The gas can then be released from the rotor 52 through vent 64 in the distribution channel 56.

Figure 2A:
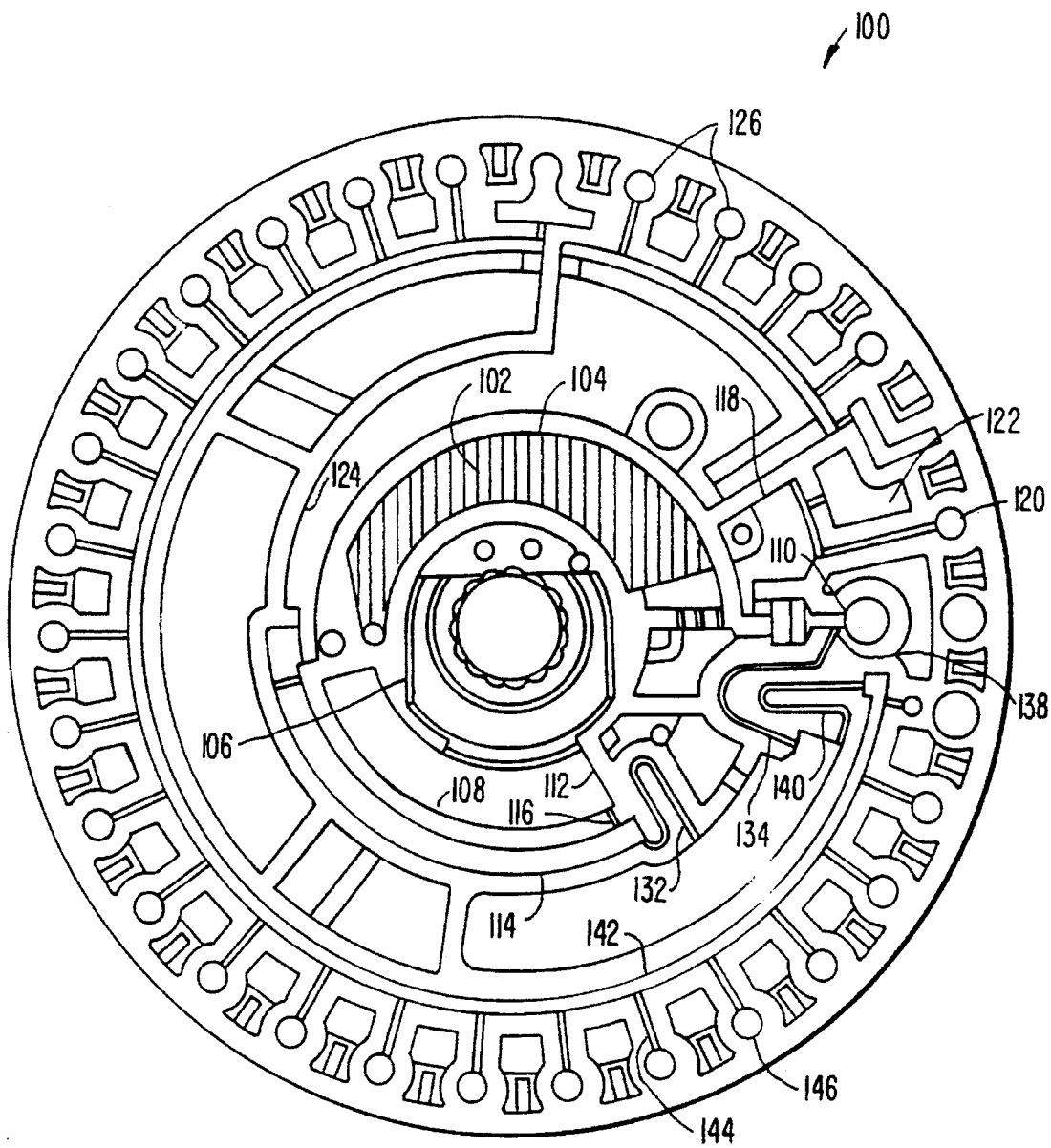
FIGS. 2A–2F are top plan views of a rotor of the invention showing the flow of fluids through the chambers and channels of the rotor as the rotor is spun.
Figure 2B:
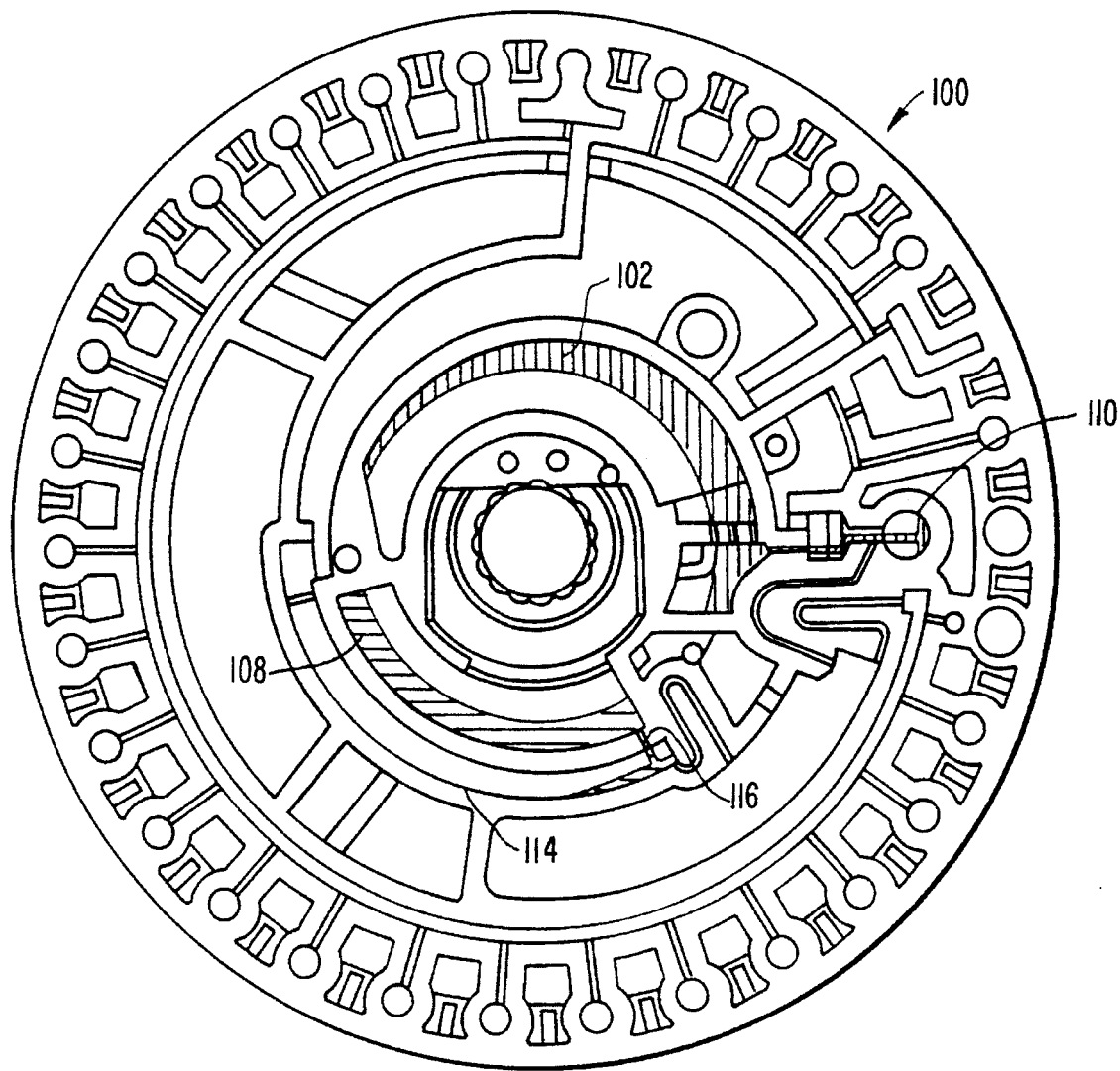
Figure 2C:
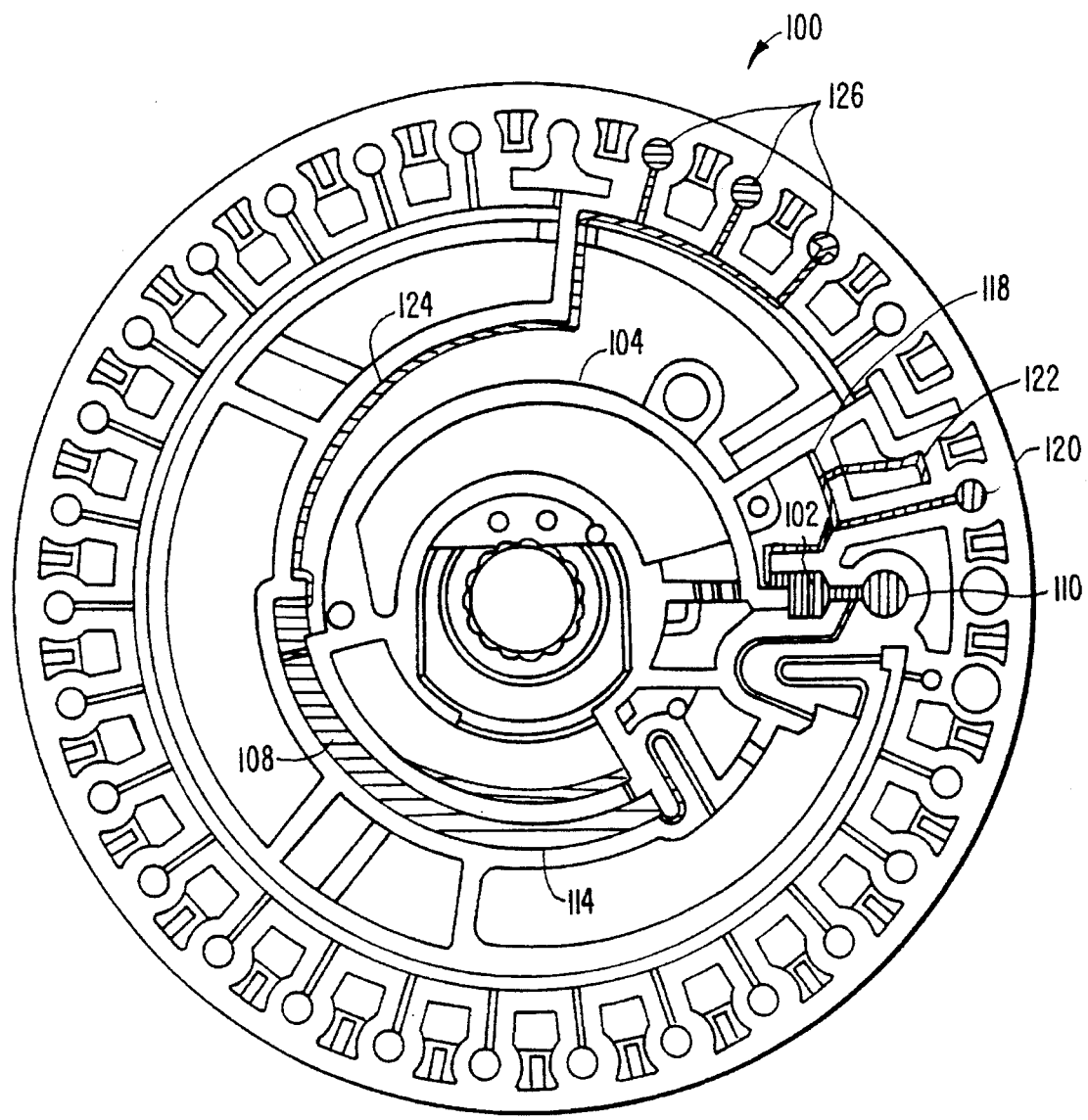

FIGS. 2A through 2F illustrate the operation of a rotor made according to the present invention. FIG. 2A shows the position of a blood sample 102 in the blood metering chamber 104 after the sample has been loaded in the rotor. A diluent container in chamber 106 is opened upon mounting of the rotor on the spindle of the centrifuge as described in copending and commonly assigned application, U.S. Ser. No. 7/873,327, which is incorporated herein by reference. FIG. B shows the position of the diluent 108 and blood sample 102 after the rotor is spun at 4,000 rpm. The blood sample 102 begins to exit the blood metering chamber 104 and enters the plasma metering chamber 110. At the same time, diluent 108 empties from the diluent container into the holding chamber 112. The diluent immediately begins to enter the diluent splitting chamber 114 through channel 116. FIG. 2C shows the position of the liquids as the rotor 100 continues to spin. Here, the blood sample 102 has emptied the blood metering chamber 104 and overflows the plasma metering chamber 110 into the overflow chamber 118 where it flows to the hemoglobin cuvette 120 and the excess blood dump 122. Meanwhile, diluent 108 fills the diluent splitting chamber 114 and excess flows through channel 124 to diluent-only cuvettes 126 and excess diluent dump 127.

Figure 2D:
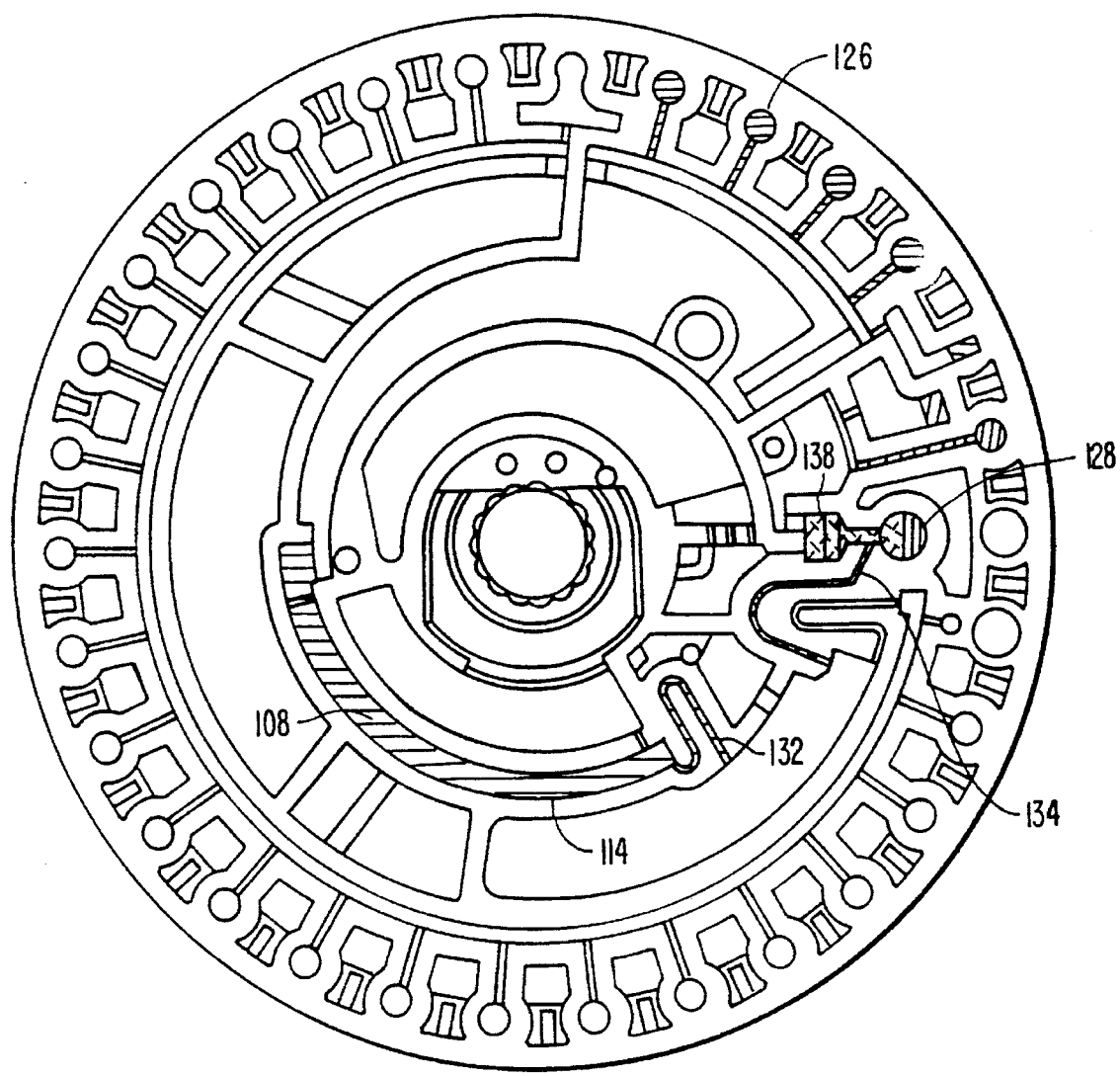

FIG. 2D shows the position of the liquids at the conclusion of the first spin. The blood sample 102 has separated into cells 128 and plasma 130. The diluent-only cuvettes 126 are filled and a predetermined amount of diluent remains in the splitting chamber 114. The rotor 100 is then stopped and the siphon 132 from the splitting chamber 114, as well as the siphon 134 from the plasma metering chamber 110, are allowed to prime, as described above.

Figure 2E:
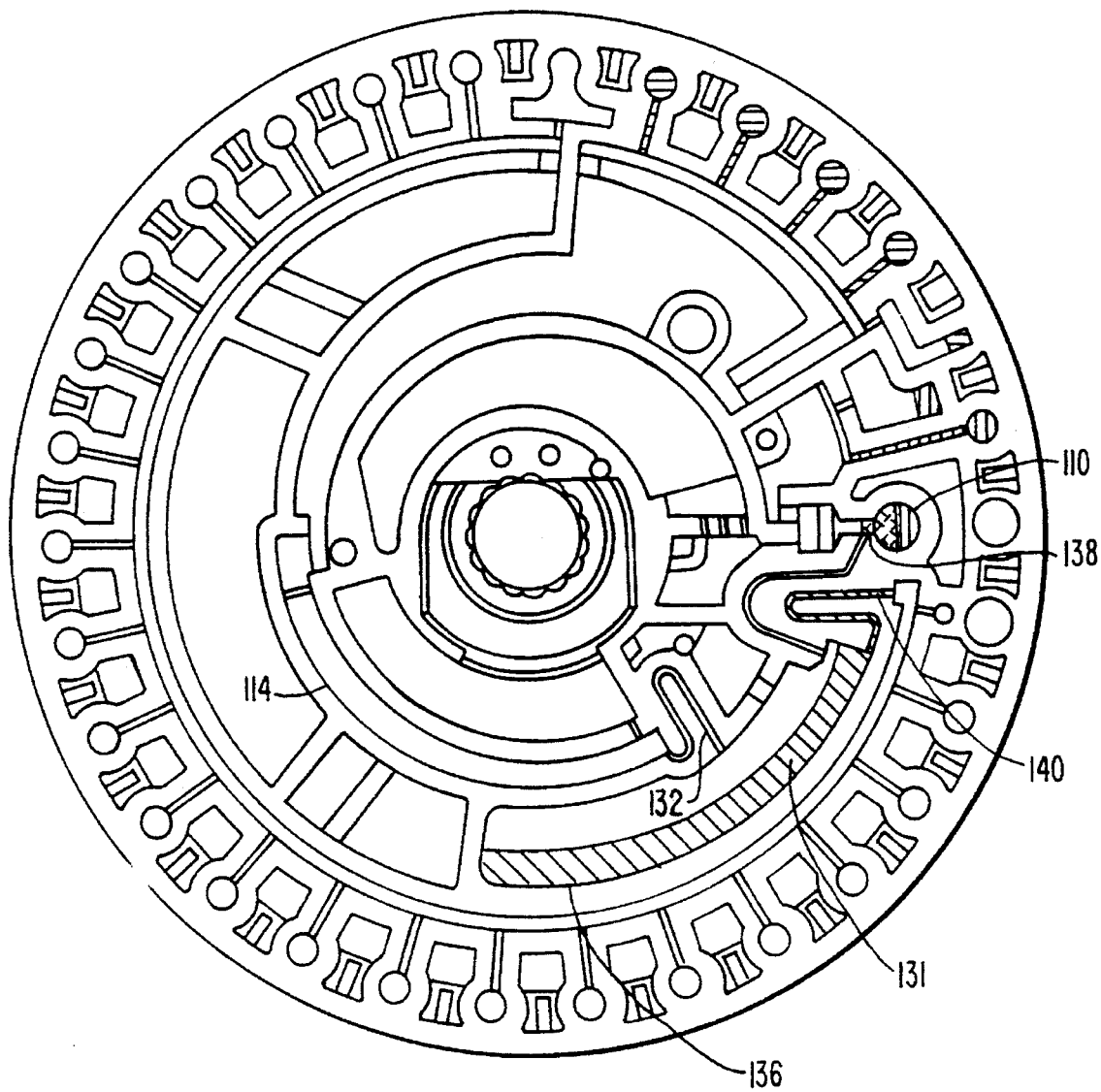

FIG. 2E shows the position of the liquids during the second spin of the rotor. The splitting chamber 114 empties into the mixing chamber 136 through siphon 132. A predetermined amount of plasma 130 is metered into the mixing chamber 136 and the two fluids are mixed, thereby forming diluted plasma 131. The amount of plasma 130 delivered to the mixing chamber 136 is determined by the position of the exit 138 on the plasma metering chamber 110. After the plasma and diluent are mixed in the mixing chamber 136, the rotor is stopped again and the output siphon 140 is primed.

Figure 2F:
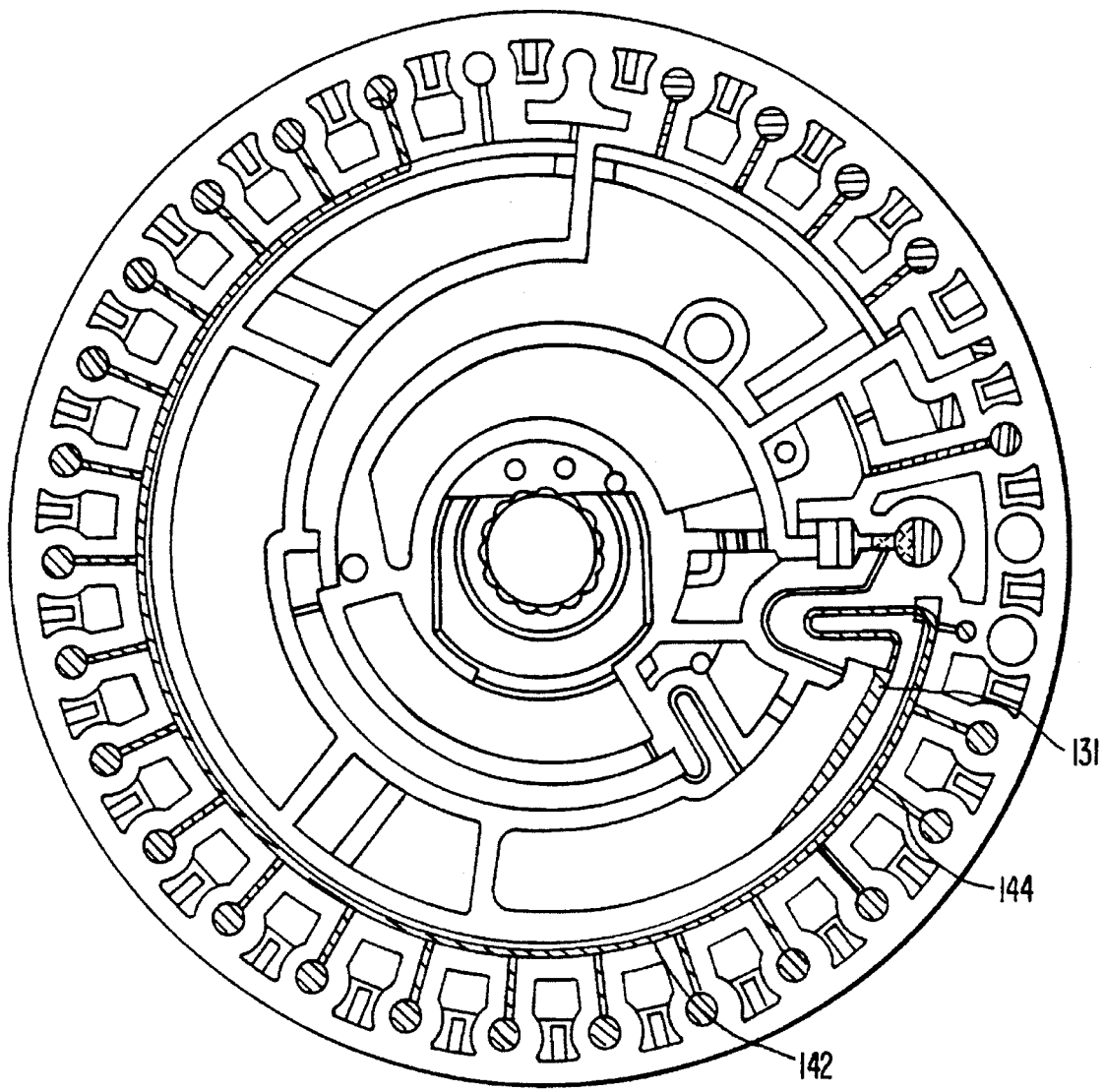

FIG. 2F shows the position of the diluted plasma 131 as the rotor is spun during the third spin. This figure illustrates the movement of the diluted plasma 131 through the distribution ring 142 and inlet channels 144 to the cuvettes 146 and excess plasma dump 147. The resistance to flow in the output siphon 140 is selected to be higher than the resistance to flow in the distribution ring 142 and the inlet channels 144 so that air present in the cuvettes 146 can escape as the cuvettes are filled. After the cuvettes have been filled, reagents present in the cuvettes are mixed with the solution and the necessary photometric analyses are made on the sample.

Although the foregoing invention has been described in detail for purposes of clarity of understanding, it will be obvious that certain modifications may be practiced within the scope of the appended claims. For instance, the liquid manifold need not be annulate. The manifold can also be used to deliver aliquots of a sample to chambers in a rotor other than cuvettes. In addition, each cuvette can be individually vented instead of using a venting manifold.

What is claimed is:

1. A centrifugal rotor comprising:

a sample chamber containing a liquid;

an unvented receiving chamber positioned radially outward from the sample chamber;

a delivery channel connected to the sample chamber for removing the liquid from the sample chamber under centrifugal force;

a distribution channel directly connected to the delivery channel for removing the liquid from the delivery channel under centrifugal force;

an inlet channel connected to the unvented receiving chamber for receiving the liquid from the sample chamber through the delivery channel and the distribution channel;

wherein, the resistance to flow of the liquid in the delivery channel is greater than the resistance to flow of the liquid in the inlet and distribution channels such that the cross-sectional area of the liquid flowing through the inlet and distribution channels is less than the cross-sectional area of said inlet and distribution channels, whereby spinning the rotor effects the flow of the liquid from the sample chamber through the delivery channel, the distribution channel and the inlet channel to the receiving chamber such that air escapes from the receiving chamber through the inlet channel as the liquid enters the receiving chamber.

2. The rotor of claim 1, wherein the receiving chamber is a cuvette containing reagents necessary for the analysis of a biological sample.

3. The rotor of claim 1, wherein the inlet channel has a cross sectional area at least about 1.5 times the cross sectional area of the delivery channel.

4. The rotor of claim 3, wherein the cross sectional area of the inlet channel is about 2 times the cross sectional area of the delivery channel.

5. The rotor of claim 3 wherein the cross sectional area of the delivery channel is about 0.03 mm$^2$.

6. The rotor of claim 1, wherein the delivery channel is a siphon.

7. The rotor of claim 1, wherein the sample chamber is a mixing chamber.

8. The rotor of claim 7, further comprising a diluent splitting chamber positioned radially inward of the mixing chamber and connected to the mixing chamber through a siphon.

9. The rotor of claim 7, further comprising a plasma metering chamber positioned radially inward of the mixing chamber and connected to the mixing chamber through a siphon.

* * * * *